United States Patent
Goldbach

(10) Patent No.: US 8,412,308 B2
(45) Date of Patent: Apr. 2, 2013

(54) MEDICAL LASER TARGET MARKER AND ITS USE

(75) Inventor: Günter Goldbach, Wörth/Wifling (DE)

(73) Assignee: Brainlab AG, Feldkirchen (DE)

( * ) Notice: Subject to any disclaimer, the term of this patent is extended or adjusted under 35 U.S.C. 154(b) by 1168 days.

(21) Appl. No.: 12/017,424

(22) Filed: Jan. 22, 2008

(65) Prior Publication Data

US 2008/0183065 A1    Jul. 31, 2008

Related U.S. Application Data

(60) Provisional application No. 60/893,282, filed on Mar. 6, 2007.

(30) Foreign Application Priority Data

Jan. 31, 2007    (EP) .................................... 07002066

(51) Int. Cl.
*A61B 5/05*       (2006.01)
(52) U.S. Cl. .......................... 600/424; 600/407; 378/206
(58) Field of Classification Search .................. 600/426, 600/429, 407, 424; 248/466, 467; 356/256; 378/206

See application file for complete search history.

(56) References Cited

U.S. PATENT DOCUMENTS

| | | | | |
|---|---|---|---|---|
| 5,831,260 | A * | 11/1998 | Hansen | 250/221 |
| 6,299,122 | B1 | 10/2001 | Bame | |
| 2003/0210812 | A1* | 11/2003 | Khamene et al. | 382/128 |
| 2004/0034282 | A1* | 2/2004 | Quaid, III | 600/300 |
| 2004/0200947 | A1* | 10/2004 | Lau | 250/202 |
| 2006/0058604 | A1 | 3/2006 | Avinash et al. | |
| 2007/0242034 | A1* | 10/2007 | Haven | 345/156 |
| 2008/0269596 | A1* | 10/2008 | Revie et al. | 600/424 |

FOREIGN PATENT DOCUMENTS

| | | |
|---|---|---|
| WO | 99/27837 | 6/1999 |
| WO | 01/43654 | 6/2001 |

* cited by examiner

*Primary Examiner* — Unsu Jung
*Assistant Examiner* — Daniel Huntley
(74) *Attorney, Agent, or Firm* — Renner, Otto, Boisselle & Sklar, LLP

(57) ABSTRACT

A medical laser target marker includes a retro-reflector for receiving and reflecting light, at least one first medical tracking marker, and at least one second medical tracking marker. The at least one first medical tracking marker is arranged on the laser target marker and has a first functional configuration. The at least one second medical tracking marker is arranged on the laser target marker and has a second functional configuration different from the first functional configuration.

18 Claims, 1 Drawing Sheet

MEDICAL LASER TARGET MARKER AND ITS USE

RELATED APPLICATIONS DATA

This application claims priority of U.S. Provisional Application No. 60/893,282 filed on Mar. 6, 2007, which is incorporated herein by reference in its entirety.

FIELD OF THE INVENTION

The invention relates to calibration and/or calibration testing for medical tracking systems and, more particularly, to a medical laser target marker and its use.

BACKGROUND OF THE INVENTION

Medical tracking systems can be used to ascertain a spatial position of tracking markers. When such markers are attached to objects, such as medical instruments and/or on patients, then the spatial position of the objects and/or patients also can be ascertained and provided to a medical navigation system, which enables image-guided surgery. Since the accuracy of such tracking systems is highly important for correct navigation, the systems are calibrated.

Calibrated systems provide precise positional data of the detected tracking markers. One problem with calibrating such tracking systems, however, is that the markers often cannot be calibrated in situ, i.e., at the site of installation in the hospital or in the operating theaters. The tracking systems have to be taken to special testing stations, where the spatial position of the calibration markers relative to installed "test" tracking systems is also known. Also, tracking systems comprising tracking markers of different functional configurations (optical passive tracking markers, optical active tracking markers, magnetic tracking markers, etc.) are calibrated or tested in different, specially provided calibration means.

SUMMARY OF THE INVENTION

A medical laser target marker in accordance with the invention comprises a laser target, such as an SMR target (spherically mounted retro-reflector target) for determining a position in three dimensional space, and at least one medical optical tracking marker of a first functional configuration. At least one other medical tracking marker of a different functional configuration is also arranged on the laser target marker.

A laser tracking technique for tracking a laser target marker in accordance with the present invention will now be described. Laser tracking systems are technical measuring systems for determining a spatial position of a so-called "target". The laser tracking system can measure two angles and a distance, and comprises a target and a laser tracker position determining unit (or "laser tracker" in the following). The laser tracker emits a laser beam to the retro-reflective target, which is held against the object to be measured. Light reflected by the target returns along its trajectory and re-enters the tracker at the same location at which it was emitted. Retro-reflective targets can be configured in different ways; one example is the SMR target, which comprises three reflection surfaces orientated at an angle of 90 degrees relative to each other and, thus, always returns a parallel beam of the same transit length. When the laser light re-enters the tracker, a part of the light will go to an interferometer, which measures the distance to the SMR.

A helium-neon laser, for example, can be used to measure the path to the reflector and back to the interferometer. Angle-determining means can be used to measure an angular orientation of the tracker on two mechanical axes, namely the azimuth axis and the elevation axis. Measuring the angles and the distance from the interferometer is sufficient to precisely localize the center of the SMR. Tracking software then can calculate a displacement that corresponds to a radius of the SMR, and thus arrives at the precise coordinates of the scanned surface.

Distance determination, which is a function of the laser tracker, can be either incremental or absolute. Incremental distance measurement can be performed using an interferometer and a frequency-stabilized helium-neon laser. The laser light can be split into two beams; one beam directly enters the interferometer, the other leaves the tracker, is reflected on the SMR, and on its return path re-enters the interferometer. The two light beams interfere in the interferometer, resulting in a change in cycle when the SMR changes its distance to the tracker by a distance corresponding to half a wavelength (e.g., approximately 0.3 microns). Electronic circuits can count the changes in cycle or changes in phase and determine the path taken.

Absolute distance measurement automatically determines the distance to the target, even when the beam has been previously interrupted. Infrared light from a semiconductor laser, for example, is reflected by the SMR and returns to the tracker, where it is converted into an electric signal. The signal is electronically analyzed to determine its transit time, which then is multiplied by the speed of light in air, and the distance between the tracker and the SMR is determined. The two types of laser tracker position measuring described herein, and any other types of laser tracking, can be used within the framework of the present invention.

It is then possible, using a laser target marker in accordance with the invention, to calibrate or test the calibration of an optical tracking system, since the accuracy of the laser tracker measurement can be used in situ to ascertain the position accuracy of the tracking system. It is also possible, using a medical laser target marker in accordance with the present invention, to measure, calibrate or test tracking systems of very different technical configurations, since a plurality of functional types of medical tracking markers can be provided on the laser target marker.

Tracking markers of more than one different functional configuration can be provided on the laser target marker, and conversely, a plurality of tracking markers of at least one or of each functional configuration can be provided. At least three tracking technologies can be combined in one target so as to allow a chosen number of measuring systems to be combined with a common reference. Additional targets such as RF antennae, radar localizing means or ultrasound markers also can be combined with the device and method in accordance with the present invention. A typical target marker in accordance with the invention can combine the systems in a multi-marker target on a three-dimensional or six-dimensional basis. Thus, the exact laser target measuring standard for testing the accuracy and performance of other tracking systems is provided.

The tracking markers of the first and/or other functional configurations can comprise or consist of groups of markers, in particular arrangements of a plurality of markers that are arranged in a predefined and characteristic way with respect to each other. One concept in accordance with the invention is to use a geometric arrangement of the different markers, wherein a center of the marker positions of different markers (of different functional configurations) is the same.

The tracking markers can be arranged on the surface of the SMR target, wherein the surface also bears the SMR reflector. Further, at least one tracking marker of at least one of the following functional configurations can be arranged on the laser target marker:

a) optical reflection tracking markers comprising a reflective coating, particularly a coating that reflects infrared radiation and, for example, which are configured as circular discs;

b) optical, actively emitting tracking markers, which in particular emit infrared radiation, such as LED tracking markers; and/or c) magnetic tracking markers, such as magnetic coils or arrangements of magnetic coils.

Also provided herein is a calibration device or calibration testing device for a medical tracking system. The device comprises an optical or magnetic spatial position detection system, such as a stereoscopic camera system or a magnetic localizing system and a laser tracker position determining unit, such as has been described above.

Another aspect of the present invention is the use of a laser target marker that comprises a position-determining laser target, such as an SMR target (spherically mounted retro-reflector target) and at least one medical tracking marker of a particular functional configuration, as a calibration or calibration testing marker for a medical tracking system. The target marker can be used as described above in different embodiments, and also the use of a calibration or calibration testing device such as has been mentioned in the above.

BRIEF DESCRIPTION OF THE DRAWINGS

The forgoing and other features of the invention are hereinafter discussed with reference to the drawing.

DETAILED DESCRIPTION

Figures 1, 2:
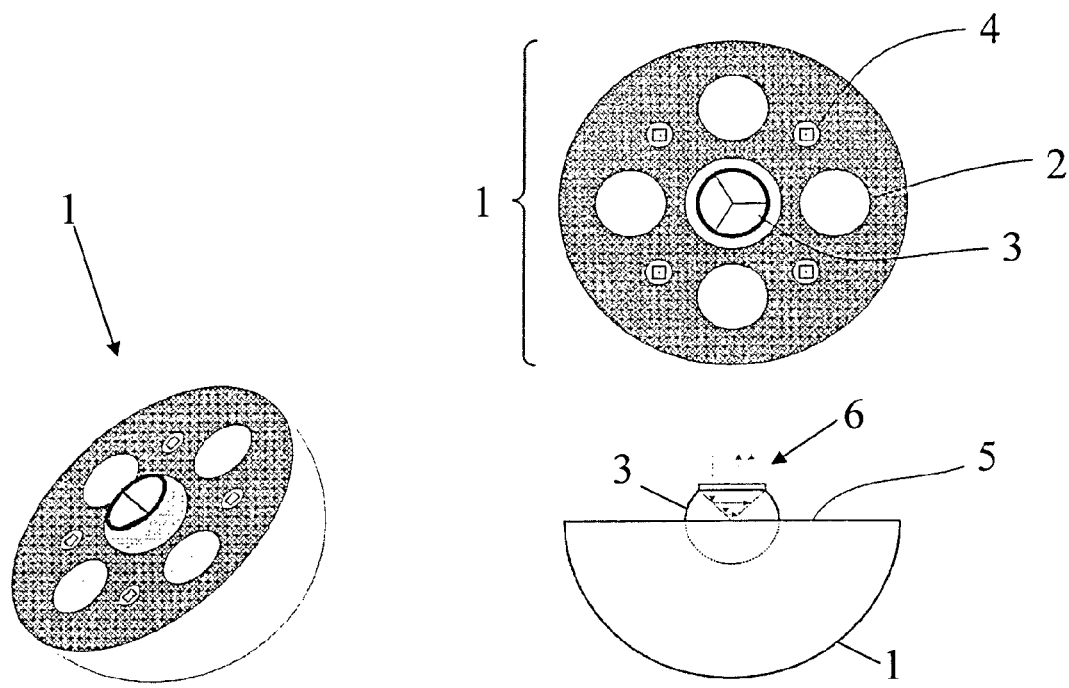
FIG. 1 is a perspective view of an exemplary laser target marker in accordance with the invention.
FIG. 2 is a top view and a lateral view of the laser target marker of FIG. 1.

An exemplary multi-marker laser target marker in accordance with an embodiment of the present invention is described with reference to FIGS. 1 and 2. The exemplary marker as a whole bears the reference sign 1 and has a substantially hemispherical shape. In the middle of its circular sectional plane 5, the marker 1 bears a so-called SMR target 3. The SMR target 3 comprises a cut sphere that protrudes out from the plane 5 and includes three reflection surfaces that are relieved towards a center portion, wherein the reflection surfaces are perpendicular to each other. Due to this arrangement of the reflection surfaces, incident light or laser beams are always reflected parallel to their direction of incidence, as shown by the reference sign 6. The reflected light returns along the same path in each case, namely always the path corresponding to a reflection at the center point of the sphere of the SMR target. Using this SMR target, it is possible to perform high-accuracy laser distance measuring, as described herein.

Additionally, other groups of tracking markers of different functional configurations are also provided on the laser target marker 1, such as a group of reflective circular disc markers, one of which is indicated by the reference sign 2, and a group of LEDs, one of which is in turn indicated by the reference sign 4. In the exemplary embodiment, four markers are provided for each of the two different tracking technologies, wherein a center of the respective arrangements of markers is in each case also the center of the SMR target 3. In an exemplary embodiment, at least two markers of each technology may be provided with a center of the arrangement in the middle of the SMR target 3. The centers of the individual markers can lie on circles around the center of the SMR target 3. Such configurations allow the center of the arrangements of tracking markers to be determined and directly compared with the location of the center of the SMR target, while simultaneously detecting the laser target marker 1 using a laser target position determining system and a medical tracking system.

Figure 3:
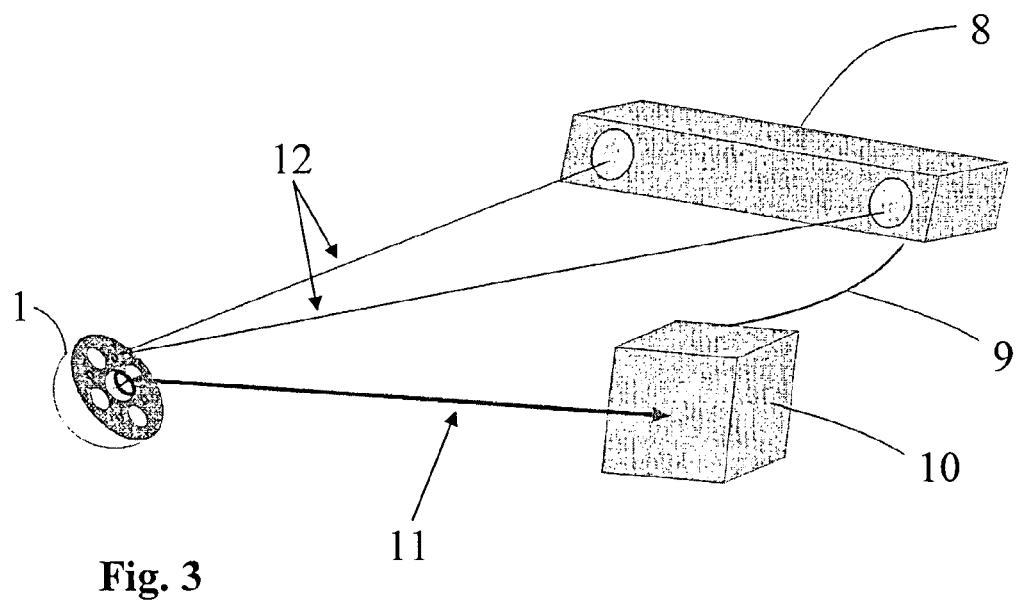
FIG. 3 a schematic representation of an exemplary calibration system in accordance with the invention for a medical tracking system.

FIG. 3 schematically shows an exemplary arrangement or typical set-up of two tracking systems coupled to each other, wherein the tracking systems use the same target, namely a laser target marker 1 such as described herein. One of the tracking systems is an optical medical tracking system 8 and the second tracking system is the laser target position determining device 10, also referred to in the introduction as the "laser tracker". The laser tracker 10 and the tracking system 8 can be connected to each other in order to compare data, as indicated by a connecting line 9. The two lines of sight 12 show how, by way of example, one of the LED markers 4 can be positionally detected by the optical tracking system 8, and the line of sight 11 shows the beam path between the laser tracker 10 and the SMR target on the laser target marker 1.

The videometric tracking system 8 (in this case, a stereoscopic system) can comprise illumination means (for example for the passive reflection markers 2). The tracking system 8 can measure the spatial position of the center of the target 1 by triangulation, e.g., by measuring the four tracking markers 4 and calculating the center of this arrangement of markers. The laser tracker 10 can measure the three-dimensional position (spatial position) of the SMR target by measuring the angles at its mounting and the distance of the target, as also described herein.

The connection 9 between the laser tracker 10 and the tracking system 8 can assume different configurations. For example, the connection can be a wireless connection or a wired connection. The connection 9 also can represent a synchronization means that ensures the measurements are obtained at the same time (which is desirable when the target 1 is moved and the positions are compared). The connection 9 also can comprise a rigid mechanical fixation between the two units, such that the relative position between the laser tracker 10 and the optical stereoscopic tracking system 8 cannot change during measurement.

On the basis of the principle described above, it is then possible to correlate the measurement of one of the two systems with the measurement of the other system. This enables the limitations (inaccuracies) of one system to be overcome, and the accuracy and performance of one system to be compared with the other. When the target 1 is moved, the relative distance between the two measuring points can be ascertained using the two systems, and errors can be detected and compensations for such errors can be made.

Unlike videometric systems, the laser tracker system forms a recognized measurement reference standard that can be attributed to physical units. The comparison between the videometric measurements and the laser tracker measurements can be used to calibrate the videometric system or to verify its accuracy and/or performance, since the positions ascertained by the laser tracker system can be directly compared with the measurements of the videometric system.

Using this technique, it is also possible to directly compare the accuracy of two different videometric systems with a (laser target) marker. This enables the performance to be precisely compared, since a large number of measuring uncertainties can be eliminated that would otherwise arise if different tracking markers were used for the different systems.

In addition to the spatial position measurement of the multi-marker target 1, it is also possible to take into account six degrees of freedom, if for example two other SMR targets are arranged on the laser target marker. It is then possible to ascertain not only the three-dimensional or spatial position of the center of the target, but also the spatial location of the target, which can be of interest for comparing angular accuracies.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A medical laser target marker device, comprising:
a marker body having a surface on which are arranged:
a retro-reflector for receiving and reflecting light;
at least one first medical tracking marker having a first functional configuration; and
at least one second medical tracking marker having a second functional configuration different from the first functional configuration;
wherein the retro-reflector, the first functional configuration and the second functional configuration correlate to three different tracking technologies, respectively.

2. The medical laser target marker device according to claim 1, wherein the at least one first medical tracking marker is an optical tracking marker.

3. The medical laser target marker device according to claim 1, wherein the retro-reflector is an SMR (spherically mounted retro-reflector) target.

4. The medical laser target marker device according to claim 3, wherein the first and second tracking markers are arranged on a surface of the SMR target.

5. The medical laser target marker device according to claim 1, wherein the at least one second medical tracking marker comprises a plurality of tracking markers, and each tracking marker of the plurality of tracking markers has a functional configuration different from other tracking markers of the plurality of tracking markers.

6. The medical laser target marker device according to claim 1, wherein the at least one first and second medical tracking markers comprise groups of markers arranged in a predefined and characteristic way with respect to each other.

7. The medical laser target marker device according to claim 1, wherein the at least one second medical tracking marker comprises:
a) optical reflection tracking markers including a reflective coating;
b) optical, actively emitting tracking markers operative to emit infrared radiation;
or
c) magnetic tracking markers.

8. The medical laser target marker device according to claim 7, wherein the reflective coating reflects infrared radiation.

9. The medical laser target marker device according to claim 7, wherein at least one second medical tracking marker is configured as a circular disc.

10. The medical laser target marker device according to claim 7, wherein the actively emitting tracking markers comprise LED tracking markers.

11. The medical laser target marker device according to claim 7, wherein the magnetic tracking markers comprise magnetic coils or arrangements of magnetic coils.

12. The medical laser target marker device according to claim 1, wherein the at least one first medical tracking marker comprises a plurality of first medical tracking markers having a first arrangement, and the at least one second medical tracking marker comprises a plurality of second medical tracking markers having a second arrangement, and wherein the retro-reflector is located at a center point of the first and second arrangement.

13. A calibration system for a medical tracking system, comprising:
a spatial position detection system;
a laser tracker position determining unit; and
the medical laser target marker device according to claim 1.

14. The calibration device according to claim 13, wherein the spatial position detection system is an optical system comprising a stereoscopic camera system.

15. The calibration device according to claim 13, wherein the spatial position detection system comprises a magnetic localizing system.

16. A method of verifying a calibration of a medical tracking system using a medical laser target marker device including i) a retro-reflector for receiving and reflecting light, and ii) at least one first medical tracking marker arranged on the laser target marker, said at least one first medical tracking marker having a first functional configuration, the method comprising:
using the retro-reflector to determine a spatial location of the medical laser target marker device;
using the at least one first medical tracking marker to determine a spatial location of the medical laser target marker device; and
if the spatial location as determined from the retro-reflector and the spatial location as determined from the at least one medical tracking marker are within a predetermined threshold, concluding that the medical tracking system calibration is within a calibration tolerance.

17. The method according to claim 16, wherein using the retro-reflector to determine the spatial location includes:
measuring a distance from a laser tracker to the retro-reflector;
determining an angular orientation of the laser tracker relative to the retro-reflector; and
determining the spatial location of the medical laser target marker based on the measured distance and the determined angular orientation.

18. The method according to claim 16, wherein the medical laser target marker device includes at least one second medical tracking marker having a second functional configuration different from the first functional configuration, wherein the retro-reflector, the first functional configuration and the second functional configuration correlate to three different tracking technologies, respectively.

* * * * *